United States Patent
Watson et al.

(10) Patent No.: US 8,480,664 B2
(45) Date of Patent: Jul. 9, 2013

(54) CONTROLLING DEPTH OF CRYOABLATION

(75) Inventors: James R. Watson, Santa Rose, CA (US); Joann Heberer, Portola Valley, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 695 days.

(21) Appl. No.: 12/687,472

(22) Filed: Jan. 14, 2010

(65) Prior Publication Data

US 2010/0179527 A1 Jul. 15, 2010

Related U.S. Application Data

(60) Provisional application No. 61/144,823, filed on Jan. 15, 2009.

(51) Int. Cl.
*A61B 18/02* (2006.01)
(52) U.S. Cl.
USPC .................................. 606/21; 606/20; 606/26
(58) Field of Classification Search
USPC ...................................................... 606/20–26
See application file for complete search history.

(56) References Cited

U.S. PATENT DOCUMENTS

| | | | |
|---|---|---|---|
| 4,483,341 A | 11/1984 | Witteles | |
| 5,147,355 A | 9/1992 | Friedman et al. | |
| 5,281,213 A | 1/1994 | Milder et al. | |
| 5,423,807 A | 6/1995 | Milder | |
| 5,632,743 A | 5/1997 | Clarke | |
| 5,759,182 A | 6/1998 | Varney | |
| 5,800,488 A | 9/1998 | Crockett | |
| 5,868,735 A | 2/1999 | Lafontaine | |
| 6,161,543 A | 12/2000 | Cox et al. | |
| 6,182,666 B1 * | 2/2001 | Dobak, III | 128/898 |
| 6,235,019 B1 * | 5/2001 | Lehmann et al. | 606/22 |
| 6,270,493 B1 * | 8/2001 | Lalonde et al. | 606/23 |
| 6,428,534 B1 * | 8/2002 | Joye et al. | 606/21 |
| 6,468,297 B1 * | 10/2002 | Williams et al. | 607/113 |
| 6,527,769 B2 | 3/2003 | Langberg et al. | |
| 6,537,271 B1 | 3/2003 | Murray et al. | |
| 6,562,030 B1 | 5/2003 | Abboud et al. | |
| 6,709,431 B2 | 3/2004 | Lafontaine | |
| 6,719,755 B2 | 4/2004 | Sliwa, Jr. et al. | |

(Continued)

OTHER PUBLICATIONS

Mazur, Peter, Cryobiology: The Freezing of Biological Systems, Science, vol. 168, May 22, 1970, pp. 939-949.

*Primary Examiner* — Linda Dvorak
*Assistant Examiner* — Amanda Scott
(74) *Attorney, Agent, or Firm* — Seager, Tufte & Wickhem, LLC

(57) ABSTRACT

A method of performing cryotherapy on a patient can include positioning an outer surface of a distal portion of a cryotherapy catheter in contact with body tissue to be treated; performing a treatment phase, including regulating a temperature of the outer surface at a treatment value for a first period of time; performing a recovery phase comprising allowing the temperature of the outer surface to warm up to a recovery value that is higher than treatment value but substantially lower than a normal body temperature of the patient; and performing one or more additional treatment phases for a second period of time. Each of the first and second periods of time can be selected to allow a cold front having a cold front temperature to propagate from the outer surface and through a therapeutic portion of a thickness of the body tissue, but not substantially beyond the thickness.

19 Claims, 5 Drawing Sheets

U.S. PATENT DOCUMENTS

| | | |
|---|---|---|
| 7,207,986 B2 | 4/2007 | Abboud et al. |
| 7,625,369 B2 * | 12/2009 | Abboud et al. ........... 606/21 |
| 7,794,454 B2 * | 9/2010 | Abboud et al. ........... 606/21 |
| 2002/0087157 A1 | 7/2002 | Sliwa, Jr. et al. |
| 2002/0111612 A1 | 8/2002 | Lalonde et al. |
| 2002/0128639 A1 | 9/2002 | Pless et al. |
| 2003/0024537 A1 | 2/2003 | Cox et al. |
| 2003/0073992 A1 | 4/2003 | Sliwa, Jr. et al. |
| 2003/0181901 A1 | 9/2003 | Maguire et al. |
| 2003/0220634 A1 | 11/2003 | Ryba et al. |
| 2004/0054363 A1 | 3/2004 | Vaska et al. |
| 2004/0176755 A1 | 9/2004 | Lafontaine |
| 2006/0178662 A1 | 8/2006 | Ripley et al. |
| 2007/0299432 A1 | 12/2007 | Arless et al. |
| 2009/0182318 A1 * | 7/2009 | Abboud et al. ........... 606/21 |
| 2009/0299355 A1 | 12/2009 | Bencini et al. |
| 2009/0299356 A1 | 12/2009 | Watson |
| 2010/0049184 A1 | 2/2010 | George et al. |
| 2010/0241113 A1 | 9/2010 | Ingle |

* cited by examiner

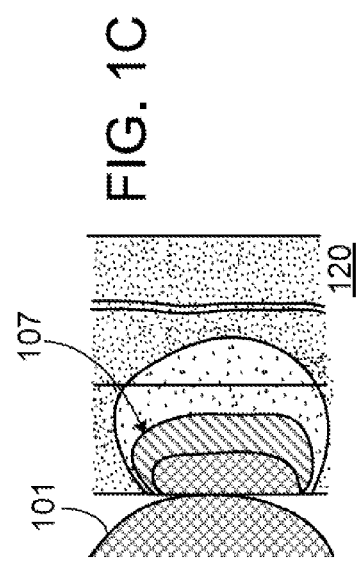
FIG. 1A
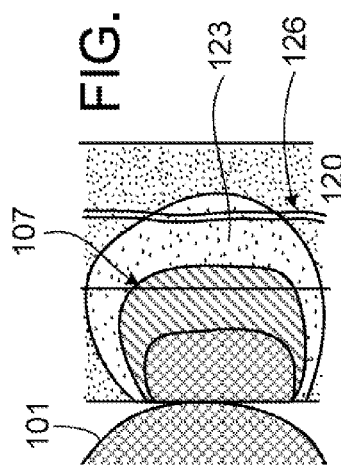
FIG. 1C
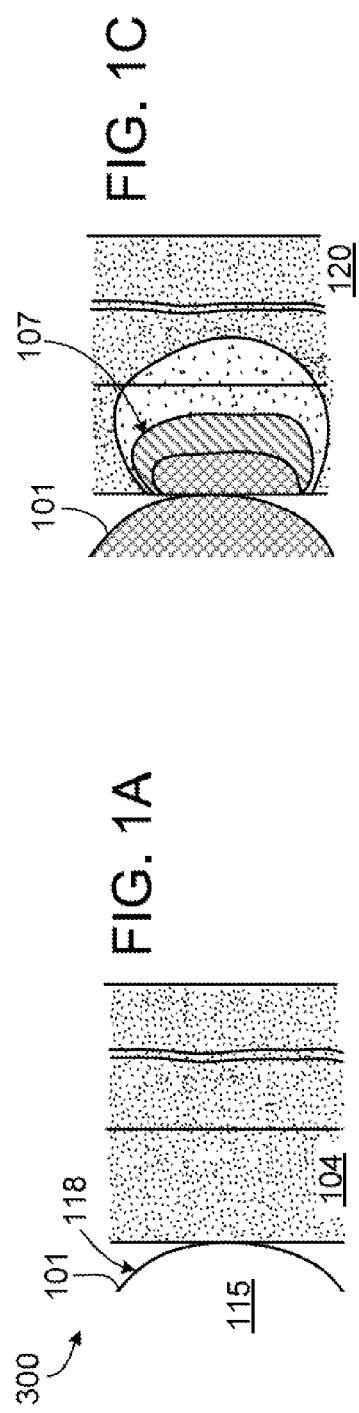
FIG. 1B
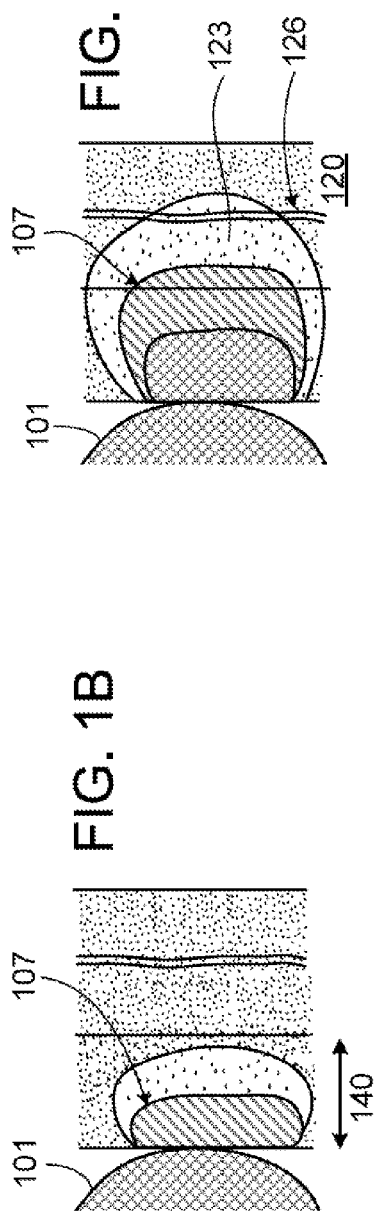
FIG. 1D
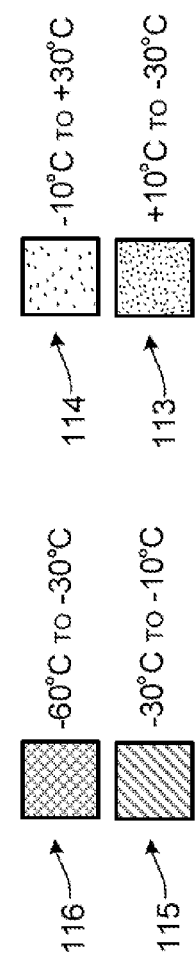

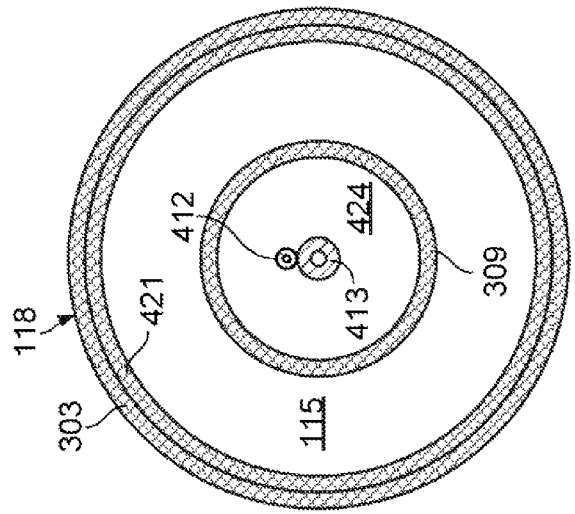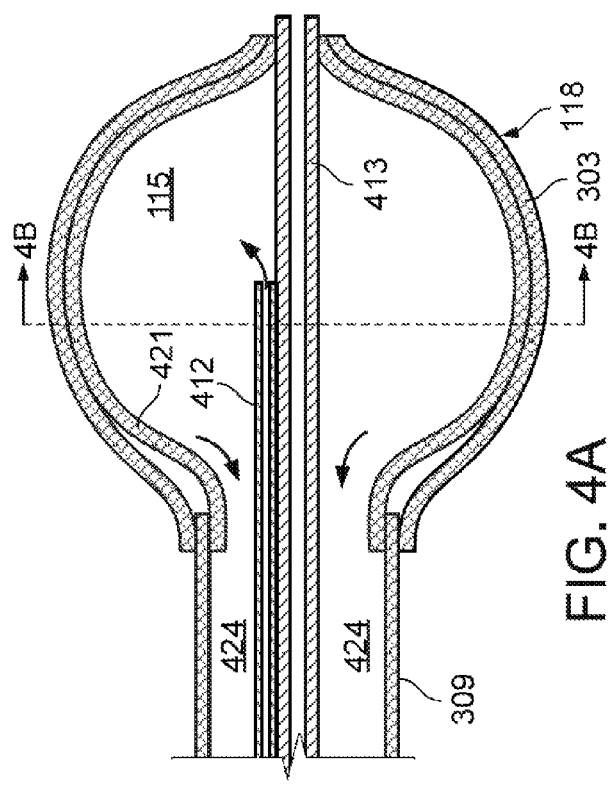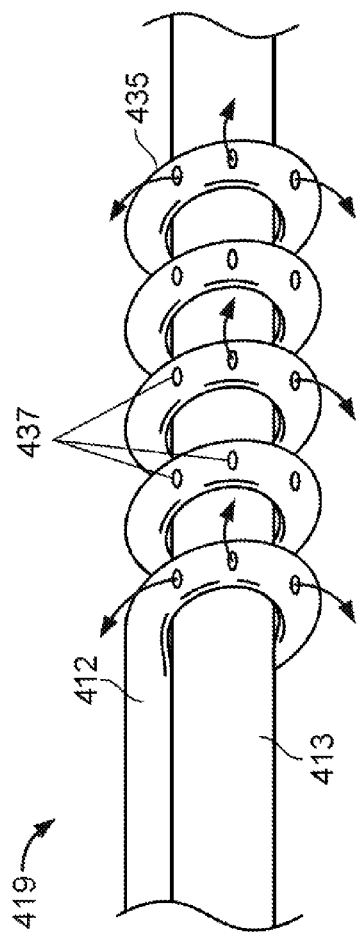

CONTROLLING DEPTH OF CRYOABLATION

CROSS-REFERENCE TO RELATED APPLICATION

This application claims priority under 35 U.S.C. §119(e) to U.S. Provisional Patent Application Ser. No. 61/144,823, filed on Jan. 15, 2009, the entire contents of which are hereby incorporated by reference.

BACKGROUND

A number of serious medical conditions may be treated in a minimally invasive manner with various kinds of catheters designed to reach treatment sites internal to a patient's body. One such medical condition is atrial fibrillation—a condition that results from abnormal electrical activity within the heart. This abnormal electrical activity may originate from various focal centers of the heart, and generally decreases the efficiency with which the heart pumps blood. It is believed that some of these focal centers reside in the pulmonary veins of the left atrium. It is further believed that atrial fibrillation can be reduced or controlled by structurally altering or ablating the tissue at or near the focal centers of the abnormal electrical activity.

One method of ablating tissue of the heart and pulmonary veins to treat atrial fibrillation is cryotherapy—the extreme cooling of body tissue. Cryotherapy may be delivered to appropriate treatment sites inside a patient's heart and circulatory system by a cryotherapy catheter. A cryotherapy catheter generally includes a treatment component at its distal end with a cooling chamber inside, such as a metal tip or an expandable balloon. A cryogenic fluid may be provided by a source external to the patient at the proximal end of the cryotherapy catheter and delivered distally through a lumen to the cooling chamber where it is released. Release of the cryogenic fluid into the chamber cools the chamber (e.g., through the Joule-Thomson effect), and correspondingly, the treatment component's outer surface, which is in contact with tissue that is to be ablated. Gas resulting from release of the cryogenic fluid may be exhausted proximally through an exhaust lumen to a reservoir or pump external to the patient.

SUMMARY

When treating targeted body tissue with cryotherapy, it can be desirable to control the depth to which the cryotherapy propagates into and beyond targeted tissue. Controlling the depth can include performing multiple treatment and recovery phases during a cryotherapy procedure. During a treatment phase, the temperature of a treatment component can be maintained at a therapeutic temperature for a first period of time that is selected to allow a cold front—having a temperature that is low enough to treat (e.g., permanently alter in some applications) the targeted tissue—to propagate from the treatment component, into the targeted tissue, to a therapeutic depth. A recovery phase can follow the treatment phase. During the recovery phase, the temperature of the treatment component can be allowed to warm up to a temperature that is higher than the therapeutic temperature but substantially lower than the normal body temperature of the targeted tissue, such that the cold front retreats back through the targeted tissue. In some implementations, after the cold front has again reached the treatment component, an additional cycle, including another treatment phase can be initiated. Multiple cycles can be performed both to deliver efficacious cryotherapy and to control the depth to which the cryotherapy is delivered.

A method of performing cryotherapy on a patient can include positioning an outer surface of a distal portion of a cryotherapy catheter in contact with body tissue to be treated and performing a treatment phase that includes regulating a temperature of the outer surface at a treatment value for a first period of time. The first period of time can be selected to allow a cold front having a cold front temperature to propagate from the outer surface and through a therapeutic portion of a thickness of the body tissue, but not substantially beyond the thickness. The method can further include performing a recovery phase that includes allowing the temperature of the outer surface to warm up to a recovery value that is higher than the cold front temperature but substantially lower than a normal body temperature of the patient; and performing an additional treatment phase for a second period of time, the second period of time selected to allow the cold front to propagate from the outer surface and through the therapeutic portion of the thickness, but not substantially beyond the thickness.

In some implementations, performing the additional treatment phase includes performing the additional treatment phase without repositioning the outer surface following the treatment phase and recovery phase. Multiple recovery phase-additional treatment phase sequences can be performed. The treatment value may be −60° C. or colder. The recovery value may be between −10° C. and +10° C. The cold front temperature may be approximately −30° C. In some implementations, the recovery value is selected such that adhesion between the body tissue and the outer surface caused by performing the treatment phase is maintained through one or more recovery cycles.

The distal portion may include an inflatable balloon. The method can further include measuring a temperature at or in close proximity to the outer surface; performing the recovery cycle can include performing the recovery cycle for a period of time determined at least in part by the measured temperature. In some implementations, the second period of time is shorter than the first period of time.

A cryotherapy catheter can include an elongate member and a treatment component disposed at a distal end of the elongate member. The elongate member can have lumens disposed therein to supply a cryogenic agent to an internal chamber of the treatment component and to channel exhaust from the internal chamber. The cryotherapy catheter can further include a controller programmed to control, during a cryotherapy procedure in which an outer surface of the treatment component is in contact with body tissue of a patient, a supply rate at which the cryogenic agent is supplied to the internal chamber and an exhaust rate at which exhaust is channeled from the internal chamber. In some implementations, the controller is programmed to (a) during a treatment phase of the cryotherapy procedure, regulate the supply and exhaust rates to cause a temperature on the outer surface to reach and be maintained at a treatment value for a first period of time that is selected to allow a cold front having a cold front temperature to propagate from the outer surface and through a therapeutic thickness of the body tissue, but not substantially beyond the therapeutic thickness; (b) during a recovery phase of the cryotherapy procedure, regulate the supply and exhaust rates to cause a temperature on the outer surface to warm up to a recovery value that is higher than the cold front temperature but substantially lower than the normal body temperature; and (c) perform an additional treatment phase for a second period of time, the second period of time selected to allow the cold front to propagate from the outer surface and through the therapeutic portion of the thickness, but not substantially beyond the thickness.

In some implementations, the cryotherapy catheter further includes a temperature sensor disposed on or in close proximity to the outer surface. The controller can be programmed to regulate the supply and exhaust rates during the recovery phase based at least in part on a temperature value measured by the temperature sensor. The treatment component can be an inflatable balloon. The inflatable balloon can be configured to deliver cryotherapy to at least one of the human patient's prostate, brain, or varicose vein. A diameter of the elongate member can be sized such that the inflatable balloon can be routed, in a deflated state, to the left atrium of an adult human patient. The inflatable balloon can be configured to deliver, when inflated, cryotherapy to an ostium or antrum of a human patient's pulmonary vein. The controller can be programmed to regulate the supply and exhaust rates during the treatment cycle in a manner that prevents damage to a phrenic nerve of the patient.

The details of one or more implementations are set forth in the accompanying drawings and the description below. Other features, objects, and advantages will be apparent from the description and drawings, and from the claims.

BRIEF DESCRIPTION OF DRAWINGS

FIGS. 1A to 1D depict a cold front propagating from a treatment component into targeted body tissue.

FIGS. 4A-4C illustrate additional details of the example cryotherapy catheter shown in FIG. 3.

Like reference symbols in the various drawings indicate like elements.

DETAILED DESCRIPTION

Figure 2:
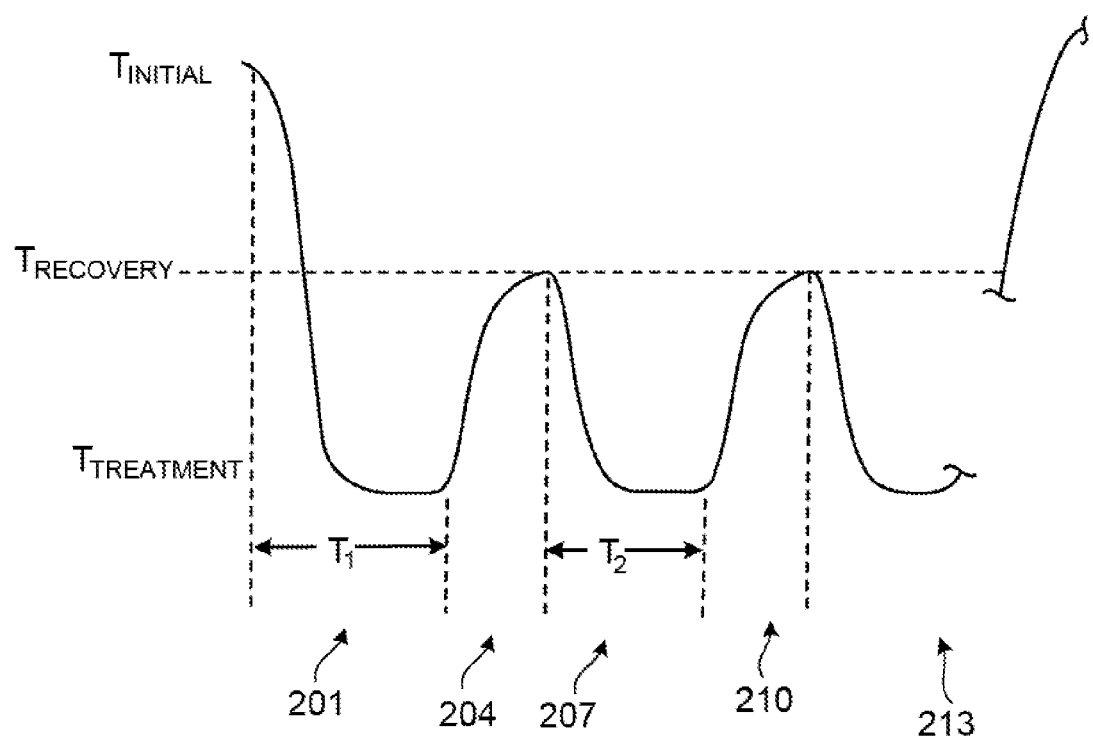
FIG. 2 illustrates an example cooling profile that can be applied to targeted body tissue.

When treating targeted body tissue with cryotherapy, it can be desirable to control the depth to which the cryotherapy propagates into and beyond targeted tissue. Controlling the depth can include performing multiple treatment and recovery phases during a cryotherapy procedure. During a treatment phase, the temperature of a treatment component can be maintained at a therapeutic temperature for a first period of time that is selected to allow a cold front—having a temperature that is low enough to treat (e.g., permanently alter in some applications) the targeted tissue—to propagate from the treatment component, into the targeted tissue, to a therapeutic depth. A recovery phase can follow the treatment phase. During the recovery phase, the temperature of the treatment component can be allowed to warm up to a temperature that is higher than the therapeutic temperature but substantially lower than the normal body temperature of the targeted tissue, such that the cold front retreats back through the targeted tissue. In some implementations, after the cold front has again reached the treatment component, an additional cycle, including another treatment phase can be initiated. Multiple cycles can be performed both to deliver efficacious cryotherapy and to control the depth to which the cryotherapy is delivered.

FIGS. 1A to 1D depict a cold front propagating from a treatment component 101. For purposes of example, the treatment component 101 is depicted as the treatment end of a cryotherapy catheter 300, which is illustrated in and described in greater detail with reference to FIG. 3. The reader will appreciate, however, that the principles described herein can be applied to devices other than catheters. For simplicity, this document describes in various places propagation of a cold front, but the reader will appreciate that propagation of a cold front may, more precisely, involve extraction of heat from progressively deeper tissue.

During a cryotherapy procedure, the treatment component 101 can be positioned in contact with the targeted tissue 104. For example, in a procedure to treat atrial fibrillation, the treatment portion 101 of a cryotherapy catheter 300 can be disposed inside a patient's heart, and more particularly, disposed at and against an ostium or antrum of one of the patient's pulmonary veins.

To deliver cryotherapy, a cryogenic agent can be delivered to a chamber 115 inside the treatment component 101, in order to cool an outer surface 118 of the treatment component 101 and, correspondingly, targeted body tissue 104 that is in contact with the outer surface 118. Cooling of the outer surface 118 causes a cold front to propagate into the targeted body tissue 104, as is depicted in and described with reference to FIGS. 1B-1D.

FIG. 1B depicts a cold front 107 that advances deeper into the body tissue 104 over time. As used herein, the cold front temperature can include a temperature that is therapeutically effective in treating (e.g., ablating) tissue. For example, some implementations involve cooling the outer surface 118 to about −60° C. or cooler, which creates a temperature gradient that includes the cold front 107 having a cold front temperature (e.g., about −30° C.) to advance into the body tissue 104. More generally, FIG. 1B depicts a temperature gradient that forms across a thickness 110 of the targeted body tissue 104 when the cooled outer surface 118 is in contact with the body tissue 104. FIGS. 1C and 1D illustrate the temperature gradient at later points in time, and further depict how the cold front 107 can penetrate deeper into the body tissue 104 over time.

As depicted, various regions of varying temperature can be formed (e.g., regions having temperatures within specific ranges, such as, for example −60° C. to −30° C., −30° C. to −10° C., −10° C. to +10° C., and 10° C. to 37° C.), example regions 113, 114, 115 and 116 of which are shown in FIG. 1B-1D. For purposes of illustration, the granularity of the temperature range within each region 113-116 is quite large, but the reader will appreciate that an actual temperature gradient may have a range of temperatures that varies substantially continuously, or in smaller steps, rather than in the larger steps depicted.

As depicted in FIGS. 1C-1D, tissue 120 beyond the targeted body tissue 104 may also be cooled, depending on how deep the cold front 107—or more generally the temperature gradient—propagates into and beyond the targeted tissue 104. This depth can depend on various factors, including, for example, the type of targeted tissue 104; the thickness 110 of that tissue; other tissue, structures, or spaces that are adjacent to the targeted tissue 104; physiology of the targeted tissue 104 and adjacent tissue 120 (e.g., a level of blood flow in either the targeted tissue or the adjacent tissue); and other factors.

In some implementations, it is advantageous to primarily limit the propagation of the cold front 107 to the thickness 110 of the targeted tissue 104. That is, therapy may be most effective, and unintended and possibly adverse side effects may be prevented or minimized, if the cold front 107 propagates to a therapeutic depth (e.g., a significant fraction of the thickness 110) but does not propagate substantially beyond the thickness 110 of the targeted tissue 104. In this context, preventing the cold front 107 from propagating substantially beyond the thickness 110 may include selecting a treatment time such that the cold front is not likely to propagate beyond the thickness 110 of the targeted body tissue by more than some percentage of the thickness 110 (e.g., 25%, 50%, 100%, 125%, etc.).

FIG. 1D depicts the cold front extending just beyond, but not substantially beyond, the thickness 110 of the targeted body tissue 104. As shown in the example of FIG. 1D, the cold front 107 is preceded by a cooler region 123 that extends farther into the adjacent tissue 120. In some implementations, cryotherapy is delivered for a period of time that is selected or calculated such that delivery of the cryotherapy is stopped when the cold front 107 reaches a point near that shown in FIG. 1D. By stopping the cryotherapy delivery at this point, cooling of tissue 120 beyond the cold front 107 can be minimized—which can be important for reasons that are now described.

FIGS. 1A-1D illustrate another tissue structure 126 disposed beyond the targeted body tissue 104 and in or beyond the adjacent tissue 120. As a concrete example, the targeted body tissue 104 could be the vessel wall of a patient's pulmonary vein, the adjacent tissue 120 could be tissue of the pericardium, and the tissue structure 126 could be a nerve (e.g., the phrenic nerve) that is disposed close to the targeted tissue 104. Certain tissue, including nerve tissue, may be particularly susceptible to damage caused by heating or cooling. Thus, in this example, the nerve 126 may be irreversibly damaged if the cold front 107 were to impinge on it. Accordingly, it can be advantageous to ensure that that cold front 107 does not impinge on the nerve 126.

To ensure that the cold front 107 does not impinge on the nerve 126, the period of time for the treatment phase can be selected or calculated such that the cold front 107 is not likely to propagate substantially beyond the thickness 110 of the targeted tissue 104. In some cases, it may be possible to detect a precise location of the cold front 107 at different points in time, and to use this information to control delivery of cryotherapy. In many other cases, however, it may not be possible to determine or measure the exact location or depth of propagation of the cold front over time. For example, it may not be possible or desirable to locate a temperature probe behind the targeted tissue, or otherwise determine the temperature of the targeted tissue at particular depths. Moreover, it may not be possible or desirable to determine in advance of a procedure the exact thickness 110 of the tissue 104 being treated, or a distance between the targeted body tissue 104 and other structures, such as the nerve 126 in the above example. In such cases, the period of time for the treatment phase can be selected based on empirical data obtained by anatomical studies, animal models, thermal modeling of targeted and adjacent tissue, etc.

Other manners of selecting the treatment phase duration can be employed as well. For example, a detectable physiological event may occur when the structure 126 is mildly cooled, and detection of such an event can be used to control delivery of cryotherapy. In particular, with reference to the above example in which the structure 126 is a nerve, the nerve's ability to conduct signals may be temporarily affected by being cooled to temperatures that are higher than those that may cause permanent damage. Accordingly, temporary paralysis of a muscle controlled by the nerve 126 (e.g., the diaphragm, in the case of the phrenic nerve mentioned above) can be detected as an indicator that the cool region 123 has reached the nerve, and the treatment phase can be stopped at that point.

The specific tissue structures described above are merely exemplary, and the reader will appreciate that in various other contexts, it may be advantageous to deliver cryotherapy to a portion of other kinds of targeted body tissue, while at the same time preventing delivery of the cryotherapy substantially beyond or outside of the targeted body tissue.

In some implementations, a method of controlling the depth of propagation of the cold front 107 during cryotherapy includes delivering multiple, controlled cycles of cryotherapy. For example, some procedures may employ the treatment component 101 to chill the body tissue 104 such that the cold front 107 propagates as shown in FIGS. 1B-1D. After a period of time that is selected to allow the cold front 107 to reach a therapeutic depth (e.g., the thickness 110 of the targeted tissue 104, or some fraction of that thickness 110), the cooling can be suspended (e.g., flow of a cryogenic agent to the treatment component 101 can be reduced or suspended), such that the cold front 107 retreats back toward the treatment component 101, as depicted by the reverse sequence of FIGS. 1D, 1C, 1B and 1A. At some point, such as when the cold front 107 reaches or nears the treatment component 101, as shown in FIG. 1A or 1B, the cooling can be resumed (e.g., flow of the cryogenic agent to the treatment component 101 can be increased or resumed), so that the cold front 107 again propagates through the targeted tissue 104.

In some implementations, performing multiple cycles of cryotherapy can be advantageous. Each cycle can include a treatment phase, during which targeted body tissue is cooled; and a recovery phase, during which targeted body tissue is allowed to warm up. Between cycles, the treatment component can be maintained in a fixed position. This process of cooling and warming targeted body tissue 104 can, in some implementations, lead to more effective treatment (e.g., permanent, therapeutic alteration) of the targeted tissue. In particular, for example, pulmonary veins may be more effectively isolated if the vein tissue is cooled and warmed more times for a shorter time period each time, rather than being cooled a fewer number of times for a longer duration each time. Moreover, performing multiple, controlled cooling cycles may facilitate more precise control over the depth to which a cold front propagates through targeted tissue. More precise control, in turn, can facilitate effective treatment of the targeted body tissue itself, and protection of other tissue or structures that are adjacent or close to the targeted body tissue. Overall procedure time may be reduced. In some implementations, the treatment and recovery phases may be performed such that targeted body tissue 104 does not fully warm up between subsequent treatment phases. Such implementations are now described in more detail with reference to FIG. 2.

FIG. 2 illustrates an example cooling profile that can be applied to targeted body tissue 104. In particular, FIG. 2 depicts a temperature profile that may correspond to the outer surface 118 of the treatment component 101 that is shown in FIGS. 1A-1D. As shown in the example of FIG. 2, the temperature starts at a first value $T_{initial}$, which may correspond to normal body temperature of the targeted body tissue 104. That is, before cryotherapy is actually delivered, the temperature of the outer surface 118 of the treatment component 101 may be at the normal body temperature of the targeted body tissue 104 against which it is disposed (e.g., 37° C.).

During a first treatment phase 201, the treatment component 101 can be cooled to a treatment temperature $T_{treatment}$. In some cryotherapy procedures, the treatment temperature $T_{treatment}$ may be close to the boiling point of a cryogenic agent (e.g., $N_2O$) and may be in the range of −50° C. to −90° C. As shown in this example, the first treatment phase 204 has a duration $T_1$, which may be determined or selected based on a time period during which the cold front 107 is likely to propagate from the treatment component 101 to a therapeutic depth of the targeted body tissue 104 (e.g., 75-125% of the thickness 110 of the targeted body tissue 104), as depicted by FIGS. 1B-1D.

A recovery phase 204 can be initiated when the cold front 107 is likely to have advanced (or, in some implementations, determined to have advanced) to an appropriate therapeutic depth. To initiate the recovery phase 204, the treatment component 101 can be allowed to warm up from the treatment temperature $T_{treatment}$ to a recovery temperature $T_{recovery}$. For example, flow of a cryogenic agent to the treatment component 101 can be reduced or suspended, such that the outer surface 118 warms to the recovery temperature $T_{recovery}$. The higher recovery temperature $T_{recovery}$ allows the cold front 107 to move back through the targeted body tissue 104, allowing that tissue 104 to warm up from its chilled state. In some implementations, the recovery phase 204 is terminated, and another treatment phase 207 is initiated, when the cold front 107 reaches the treatment component 101. For example, the recovery phase 207 may be terminated when a determined temperature of the body tissue 104 in close proximity to the outer surface 118 is no longer colder than the recovery temperature $T_{recovery}$. In other implementations (not shown), the recovery temperature $T_{recovery}$ may be maintained for some period of time (e.g., 10-60 seconds) before another treatment phase is initiated.

Although the recovery temperature $T_{recovery}$ is warmer than the treatment temperature $T_{treatment}$, the recovery temperature $T_{recovery}$ is, in some implementations, substantially cooler than the initial temperature $T_{initial}$ (e.g., the normal body temperature of the targeted tissue). In particular, for example, the recovery temperature $T_{recovery}$ may typically be 25° C. or more cooler than the initial temperature $T_{initial}$. Thus, for targeted tissue having an initial temperature of 37° C., the recovery temperature may be +10° C. or cooler. More particularly, for human patients, the recovery temperature may generally be in the range of −10° C. to +10° C., and in some implementations, the recovery temperature is close to or below 0° C.

Setting the recovery temperature at a value that is substantially lower than the initial temperature $T_{initial}$ (e.g., normal body temperature of the targeted tissue) and substantially higher than the treatment temperature $T_{treatment}$ (e.g., −60° C.) can result in one or more of the following advantages. As indicated above, the targeted tissue 104 can warm up enough between subsequent treatment phases that efficacy of the cryotherapy procedure can be increased. Not allowing the tissue 104 to warm up all the way to or close to its starting point $T_{initial}$ can facilitate more precise control over the extent to which a cold front 107 propagates through or beyond the targeted body tissue 104. In some implementations, maintaining during a recovery phase 204 the temperature of the interface between the treatment component 101 and the targeted tissue 104 at or just below the freezing point of the targeted tissue 104 (e.g., between 0° C. and −10° C.) can maintain adhesion between the treatment component 101 and the targeted tissue 104, thereby anchoring the position of the treatment component 101 against the targeted tissue 104 between treatment phases.

As indicated above, a first recovery phase 204 can be followed by another treatment phase 207 and recovery phase 210, and this cycle can be repeated one or more times, until a final recovery phase 213, during which the temperature of the targeted tissue 104 is allowed to warm back up to is starting value $T_{initial}$. Durations of each recovery phase can be controlled based on temperature feedback (e.g., from a temperature sensor that is disposed at or near the outer surface) or other feedback. Durations of treatment phases can be determined in advance, based on previously gathered empirical data for similar body tissue as that targeted in the cryotherapy procedure. In some cases, durations of treatment phased can be directly controlled in response to feedback, such as temperature feedback, feedback associated with a physiological event (e.g., change in muscle function suggestive of a temporarily paralyzed nerve), feedback from a measurement or determination of an amount of heat energy that is extracted from the treatment component, such as based on rates of flow of cryogenic agent to and from the treatment component, etc. In some implementations, the duration $T_1$ of a first treatment phase is longer than a duration $T_2$ of a subsequent treatment phase—given that additional cooling is generally required in the first treatment phase to cool the targeted tissue 104 from the initial temperature $T_{initial}$ to the recovery temperature $T_{recovery}$, then to cool the target tissue 104 from the recovery temperature $T_{recovery}$ to the treatment temperature $T_{treatment}$ in subsequent treatment phases.

Figure 3:
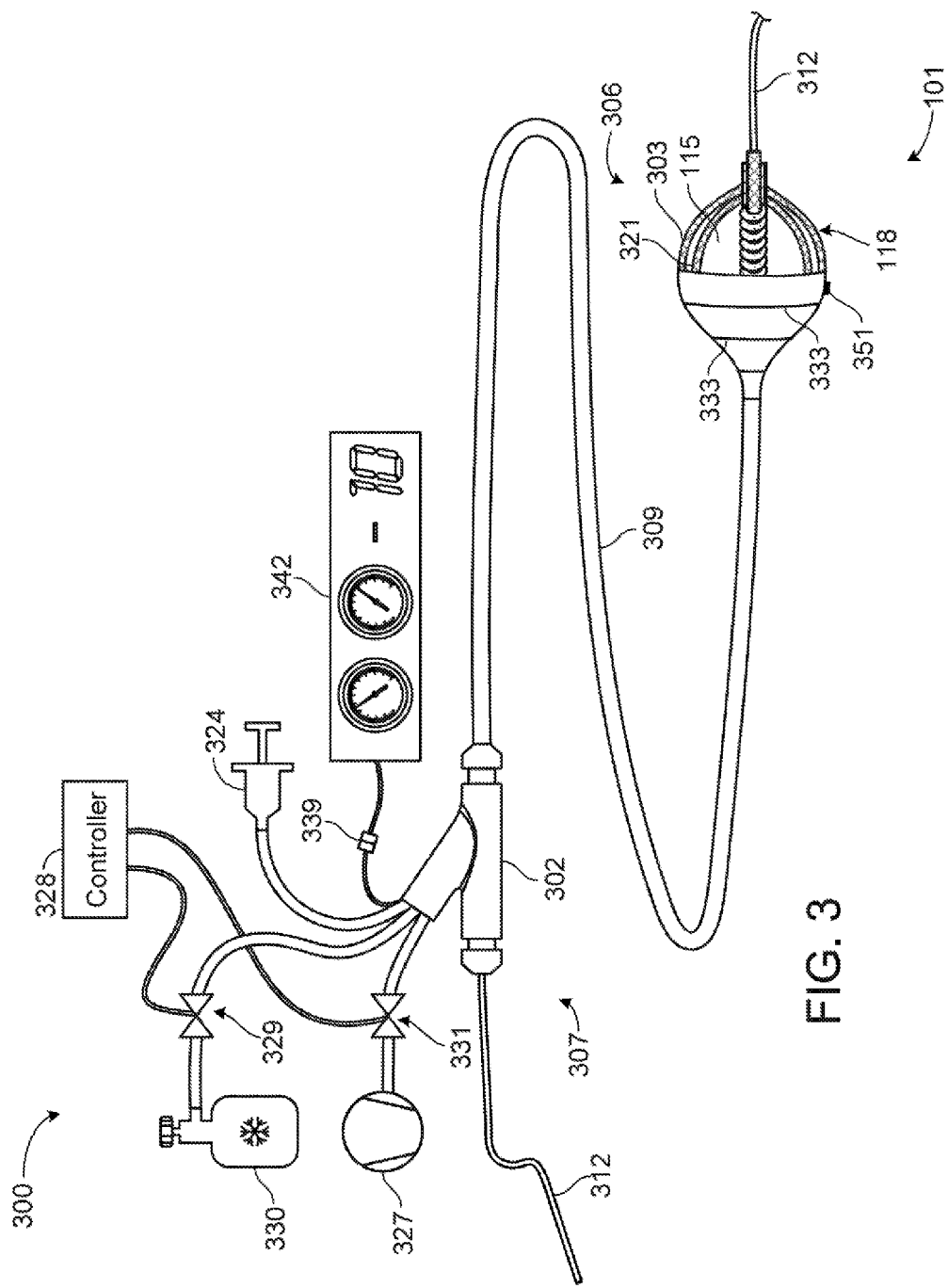
FIG. 3 illustrates details of an example cryotherapy balloon catheter that can be employed to deliver cryotherapy in the manner depicted in FIG. 2.

FIG. 3 illustrates one example treatment system that can be employed to deliver cryotherapy. The example treatment system is depicted as a cryotherapy balloon catheter 300, but the reader will appreciate that cryotherapy can be delivered by other types of catheters (e.g., solid-tip catheters), or by devices other than catheters (e.g., devices for delivering cryotherapy to external body tissue of a patient).

The cryotherapy catheter 300 can include an elongate member 309 that has a treatment component 101 (e.g., an inflatable balloon 303) at a distal end 306. The balloon 303 has an internal chamber 115 to which cryogenic fluid is delivered to cool the internal chamber, an outer surface 118 of the balloon 303, and adjacent body tissue. A port device 302 is attached to the proximal end 307 of the elongate member 309. The port device 302 provides connections to various external equipment, including a cryogenic fluid source 330 and an exhaust pump 327.

The catheter's elongate member 309 has multiple internal lumens (shown in FIGS. 4A-4C). The lumens allow cryogenic fluid to be delivered distally from the external cryogenic fluid source 330 to the internal chamber 115 of the balloon 303. In addition, the internal lumens of the elongate member 309 allow exhaust resulting from delivery of cryogenic fluid to the internal chamber 115 to be delivered proximally, from the internal chamber 115, to the external exhaust pump 327. During operation, there may be continuous circulation within the elongate member 309 of cryogenic fluid distally and exhaust proximally.

A controller 328 can regulate flow of cryogenic fluid to the internal chamber 115 of the balloon 303 and flow of exhaust from the balloon 303. In particular, for example, the controller 328 can, in one implementation as depicted, regulate a valve 329 that controls flow of the cryogenic fluid from the cryogenic fluid source 330. The cryogenic fluid source 330 may be, for example, a pressured flask of cryogenic fluid. In other implementations (not shown), the controller 328 controls a pump and/or pump valve combination to deliver cryogenic fluid to the internal chamber of the balloon. Similarly, the controller 328 can regulate a valve 331 and/or vacuum pump 327 to regulate flow of exhaust from the internal chamber of the balloon.

By controlling both the rate at which cryogenic fluid is delivered to the balloon 303 and the rate at which exhaust is extracted from the balloon 303, the controller 328 can develop and maintain a temperature on the outer surface 118 of the balloon at a number of different values. For example, when cryogenic fluid is delivered at a very low rate to the balloon 303, and exhaust is similarly extracted at a very low rate, the balloon 303 may be inflated, but very little heat (if any) may be extracted from the balloon 303 or from body tissue that is in contact with the balloon; when cryogenic fluid is delivered at a moderate rate, and exhaust is extracted at a correspondingly moderate rate, some amount of heat can be extracted from the balloon 303 and from body tissue that is in contact with the balloon; and when cryogenic fluid is delivered at a high rate, and exhaust is extracted at a correspondingly high rate, a substantial amount of heat can be extracted from the balloon 303 and from body tissue that is in contact with the balloon. Thus, by varying the rates at which cryogenic fluid is delivered and exhaust is extracted, the controller 328 can initiate different phases of cryotherapy, such as, for example, an initial phase during which the balloon 303 is merely inflated, a treatment phase 201 during which a large amount of heat is extracted from adjacent body tissue, and a recovery phase 204 during which a smaller or equal amount of heat is extracted than is restored by normal body processes (e.g., cell metabolism or perfusion).

To precisely control pressures, flow rates, and corresponding temperature, the controller 303 may employ either or both of open- or closed-loop control systems. For example, in some implementations, a rate at which cryogenic fluid is supplied (e.g., the position of the valve 329) may be controlled with an open-loop control system, and a rate at which exhaust is extracted from the balloon 303 (e.g., the position of the valve 331 or force exerted by the pump 327) may be controlled with a closed-loop control system. In other implementations, both rates may be controlled by closed-loop control systems. In a closed-loop control system, some feedback mechanism is provided. For example, to control the rate at which exhaust is extracted from the balloon 303, the controller 328 may employ an exhaust flow device (not shown), a pressure sensor (not shown) inside the balloon 303 or elsewhere in the system, or another feedback sensor, such as a temperature probe 351.

The temperature probe 351 may take many different forms. For example, the temperature probe 351 can be a thermocouple that is disposed on the outer surface 118 of the balloon 303 at a position in which it will contact targeted body tissue 104 that is adjacent to the outer surface 118. In some implementations, a number of temperature-sensing devices can be disposed along a circumference of the balloon 303, such that temperature of adjacent body tissue can be measured regardless of rotational orientation of the balloon 303. In some implementations, a temperature-sensing device can be disposed in close proximity to, but not directly on, the outer surface 118. For example, a radiation thermometer may be disposed at the distal end of the elongate member 309, near the proximal portion of the balloon 303; or, such a device may be disposed near a distal tip of a guidewire lumen (a guidewire and corresponding guidewire lumen are described below). Thermocouples and radiation thermometers are two example temperature-sensing devices, but any suitable temperature-sensing or temperature-determining (e.g., thermal-imaging) device can be employed to determine temperature of body tissue that is being treated by the treatment component 303 and provide this determined temperature to the controller 328 or other system control element.

The controller 328 itself can take many different forms. In some implementations, the controller 328 is a dedicated electrical circuit employing various sensors, logic elements, and actuators. In other implementations, the controller 328 is a computer-based system that includes a programmable element, such as a microcontroller or microprocessor, which can execute program instructions stored in a corresponding memory or memories. Such a computer-based system can take many forms, may include many input and output devices, and may be integrated with other system functions, such as the monitoring equipment 342, a computer network, other devices that are typically employed during a cryotherapy procedure, etc. For example, a single computer-based system may include a processor that executes instructions to provide the controller function; display imaging information associated with a cryotherapy procedure (e.g., from an imaging device); display pressure, temperature, and time information (e.g., elapsed time since a given phase of treatment was started); and serve as an overall interface for the cryotherapy catheter 300. In general, various types of controllers are possible and contemplated, and any suitable controller 328 can be employed.

The catheter 300 shown in FIG. 3 is an over-the-wire type catheter. Such a catheter 300 includes a guidewire 312, extending from the distal end of the catheter 100. In some implementations, the guidewire 312 may be pre-positioned inside a patient's body, and once the guidewire 312 is properly positioned, the balloon 303 (in a deflated state) and the elongate member 309 can be routed over the guidewire 312 to a treatment site. In some implementations, the guidewire 312 and balloon portion 303 of the catheter 300 may be advanced together to a treatment site inside a patient's body, with the guidewire portion 312 leading the balloon 303 by some distance (e.g., several inches). When the guidewire portion 312 reaches the treatment site, the balloon 303 may then be advanced over the guidewire 312 until it also reaches the treatment site. Other implementations are contemplated, such as steerable catheters that do not employ a guidewire. Moreover, some implementations include an introducer sheath (not shown) that can function similar to a guidewire, and in particular, that can be initially advanced to a target site, after which other catheter portions can be advanced through the introducer sheath.

The catheter 300 can include a manipulator (not shown), by which a medical practitioner may navigate the guidewire 312 and/or balloon 303 through a patient's body to a treatment site. In some implementations, release of cryogenic fluid into the cooling chamber may inflate the balloon 303 to a shape similar to that shown in FIG. 3. In other implementations, a pressure source 324 may be used to inflate the balloon 303 independently of the release of cryogenic fluid into the internal chamber of the balloon 303. The pressure source 324 may also be used to inflate an anchor member on the end of the guidewire 312 (not shown).

The catheter 300 includes a connector 339 for connecting monitoring equipment 342. The monitoring equipment may be used, for example, to monitor temperature or pressure at the distal end of the catheter 300. To aid in positioning the treatment component 303 of the catheter 300 inside a patient's body, various marker bands 333 are also disposed at the distal end 306 of the catheter 300. The marker bands 333 may be opaque when the catheter is viewed by x-ray or other imaging techniques.

In some implementations, the balloon 303, and a corresponding separate internal safety balloon, if present (e.g., balloon 421, shown in FIG. 4A), may be formed from a polymer including, but not limited to, polyolefin copolymer, polyester, polyethylene teraphthalate, polyethylene, polyether-block-amide, polyamide (e.g., nylon), polyimide, latex, or urethane. For example, certain implementations of the balloon 303 comprise PEBAX® 7033 material (70D poly ether amide block). The balloon 303 may be made by blow-molding a polymer extrusion into the desired shape. In some implementations, the balloon 303 may be constructed to expand to a desired shape when pressurized without elastically deforming substantially beyond the desired shape.

A number of ancillary processes may be used to affect the material properties of the balloon 303. For example, the polymer extrusion may be exposed to gamma radiation which can alter the polymer infrastructure to provide uniform expansion during blow molding and additional burst strength when in use. In addition, the molded balloon 303 may be exposed to a low temperature plasma field which can alter the surface properties to provide enhanced adhesion characteristics. Those skilled in the art will recognize that other materials and manufacturing processes may be used to provide balloon 303 (and any internal balloon(s)) suitable for use with the catheter.

FIG. 4A shows a longitudinal cross-section of the example cryotherapy balloon 303 and example elongate member 309 through which cryogenic fluid and exhaust may be cycled to and from an internal chamber 115 of the cryotherapy balloon 303. As depicted in FIG. 4A, cryogenic fluid may be delivered from an external source (e.g., 330 in FIG. 3) to the cooling chamber 115 internal to the balloon 303, via a coolant delivery lumen 412. The coolant may be released into the cooling chamber 115 from an opening at the end of the delivery lumen 412, or the coolant may be released through a cryotherapy device 419 (see FIG. 4C) disposed at the end of the delivery lumen 412. In some implementations, the cooling device 419 includes a coiled extension 435 having a number of apertures 437 through which pressurized liquid coolant can escape and change state to a gas. In some implementations, an exhaust lumen 424 may be defined generally by the outer layer of the elongate shaft 309, as shown. In other implementations, the catheter may include one or more dedicated exhaust lumen structures (not shown) that are defined independently of the elongate member 309.

In some implementations, as described above, the coolant undergoes a phase change within the internal chamber 115, cooling the chamber 115 via the Joule-Thomson effect, as well as cooling the external surface 118 of the outermost balloon 303 and a patient's body tissue that is adjacent to the external surface 118 of the outer balloon. In other implementations, cryogenic fluid is applied to (e.g., sprayed against) the walls of the cooling chamber, where it vaporizes, directly cooling the chamber wall and the external surface 118. The cryogenic fluid, or gas if the fluid has undergone a phase change, is then exhausted through an exhaust lumen 424 to a reservoir, pump, or vacuum source external to the catheter (e.g., 327 in FIG. 3). In some implementations, there is a continuous cycle of cryogenic fluid to the cooling chamber 115 via the delivery lumen 412 and exhaust from the cooling chamber 115 via the exhaust lumen 424.

The coolant that is cycled into the balloon 115 can be one that will provide the appropriate heat transfer characteristics consistent with the goals of treatment. In some implementations, liquid $N_2O$ may be used as a cryo coolant. When liquid $N_2O$ is used, it may be transported to the cooling chamber 115 in the liquid phase where it changes to a gas at the end of the coolant delivery lumen 412, or from the apertures 437 of a cooling device 419. Other implementations may use Freon, Argon gas, and $CO_2$ gas, or other agents, as coolants. Still other implementations may use liquid coolant, and the temperature or pressure of the liquid coolant may be controlled in a manner appropriate to achieve the desired therapeutic effect.

In some implementations, as shown, a second balloon 421 is provided within the outer balloon 303 to isolate the cryogenic fluid within the cooling chamber 115. In these implementations, the outer balloon 303 forms a safety chamber that prevents coolant from escaping if the cooling chamber 115 balloon 421 bursts. A separate vacuum lumen (not shown) may be provided to evacuate any gas or liquid that escapes from the internal cooling chamber 115. In operation, the outer and inner balloons 303 and 421 may expand and deflate together. In some implementations, release of coolant inflates the balloons 303 and 421. In some implementations, the balloons 303 or 421 are first inflated by the injection of an inflation fluid or gas (e.g., a saline solution or an inert gas), after which the coolant may be introduced to the cooling chamber 115.

In over the-wire implementations, the cryotherapy catheter 300 includes a guidewire lumen 413, which allows the balloon 303 to be routed to a treatment site inside a patient over a pre-positioned guidewire.

FIG. 4B shows a radial cross-section along the line A-A that is shown in FIG. 4A. As shown in FIG. 4B, the coolant delivery lumen 412 is adjacent to the guidewire lumen 413, and the guidewire lumen 413 is shown to be substantially coaxial with the exhaust lumen 424, which corresponds to the overall shaft (e.g., elongate member 309) of the catheter. In some implementations, lumens may have other arrangements, and more or fewer lumens may be included in the catheter. For example, the coolant delivery lumen 412 may be disposed coaxially around the guidewire lumen 413; the guidewire lumen 413 may be omitted in a steerable catheter design; lumens for steering members may be provided; one or more vacuum lumens may be included; one or more exhaust lumens may be included that are independent of the outer layer of the catheter shaft 309; additional lumens may be provided for inflating or deflating the balloons 303 or 421 or for inflating or deflating other balloons not shown in FIG. 4A; and additional lumens may be provided to control an anchor member that may be disposed on a guidewire near the distal portion of the balloon 303.

Figure 5:
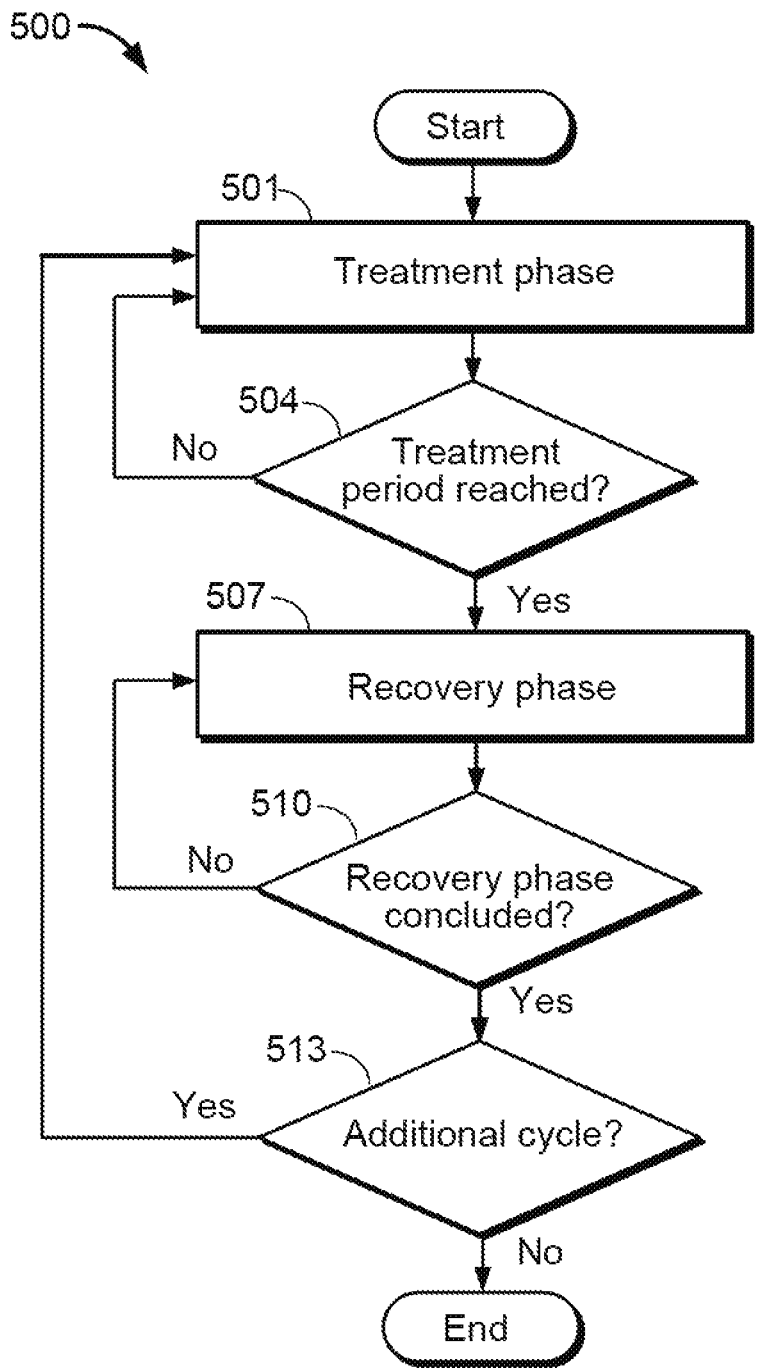
FIG. 5 is a flow diagram depicting an example method of delivering cryotherapy.

FIG. 5 is a flow diagram illustrating an example method 500 of delivering cryotherapy. In some implementations, the method 500 is implemented by the cryotherapy delivery system 300 shown in FIG. 3 and controlled by the controller 328 that is shown in the same figure.

As shown in one implementation, the method 500 includes a treatment phase 501. With reference to the previous figures, the treatment phase 501 can include positioning the treatment component 101 of the cryotherapy delivery system 300 against targeted body tissue 104, and delivering cryotherapy during a first phase 201. More specifically, during the treatment phase 501, the controller 328 can control the valve 329 to delivery a cryogenic agent from a source 330 to the distal treatment component 101, and in particular, to an internal chamber 115 of the distal treatment component 101. The controller 328 may also regulate a vacuum pump 327 and or valve 331 to exhaust an appropriate amount of cryogenic agent from the internal chamber, such that an appropriate amount of cryogenic agent is circulated through the treatment component 101 to maintain the external surface 118 at a treatment temperature $T_{treatment}$.

A determination 504 can be made as to when a treatment period has been reached. More specifically, the controller 328 can determine when cryotherapy has been delivered for the period $T_1$. As described above, this period can be selected to allow the cold front 107 to propagate through a therapeutically appropriate portion of the thickness 110 of the targeted body tissue 104, but not substantially beyond that portion. In some implementations, progress of the cold front 107 may be directly monitored (e.g., with a temperature probe) or indirectly monitored (e.g., by monitoring for a detectable physiological event that indicates progress of the cold front 107, or a cool region 123 that precedes the cold front 107). In other implementations, the duration $T_1$ of an initial treatment phase is controlled in an open-loop manner, based, for example, on thermal simulations or empirical data previously gathered for tissue that is similar to the targeted tissue 104.

After it is determined (504) that the treatment phase should be concluded, the method 500 can include initiating a recovery phase 507. During the recovery phase, the controller 328 can cause the rates to be adjusted at which the cryogenic agent is delivered to the treatment component and exhaust is extracted from the treatment component. More specifically, the rates can be adjusted such that the temperature of the external surface 118 is allowed to increase, causing the targeted tissue 104 to warm back up (and more specifically, causing the cold front 107 to retreat back through the targeted tissue 104). Some flow of cryogenic agent can be maintained during the recovery phase 507 in order to keep the external surface 118 at a temperature that, while higher than the treatment temperature $T_{treatment}$, is still substantially lower (e.g., lower by 25° C. or more) than the initial temperature $T_{initial}$. As indicated above, maintaining the recovery temperature at substantially below the initial temperature $T_{initial}$ can facilitate more efficacious cryotherapy and better control over the depth to which the cold front 107 propagates into and beyond the targeted tissue 104.

In some implementations, the recovery phase 510 is concluded when the cold front 107 moves back through the targeted tissue 104 to, or near, the external surface 118. Such a state can be detected by a temperature probe, such as the probe 351. More specifically, the temperature probe can detect when the temperature of the targeted tissue reaches or rises above the recovery temperature $T_{recovery}$. At such a point, a determination can be made (513) whether an additional treatment cycle should be initiated. In other implementations, the recovery phase is maintained beyond a point at which the cold front 107 has reached the treatment component 101. For example, the recovery temperature $T_{recovery}$ can be maintained for some additional period of time.

If it is determined (513) that an additional cycle is desired, another treatment phase 501 can be initiated. That is, flow of the cryogenic agent to and from the treatment component can be resumed or increased, such that the external surface 118 again drops to the treatment temperature $T_{treatment}$, causing the cold front 107 to again propagate through the targeted tissue 104. Additional treatment phases 501 may be carried out as indicated above, although, as previously mentioned, their duration, $T_2$, may be shorter than the duration $T_1$ of the initial treatment phase, since the temperature swing from the recovery temperature $T_{recovery}$ to the treatment temperature $T_{treatment}$ less than the temperature swing between the initial temperature $T_{initial}$ and the treatment temperature $T_{treatment}$. A number of cycles of treatment and recovery phases can be performed, after which the temperature of the external surface 118 can be allowed to warm back up to the initial temperature $T_{initial}$ during a final recovery phase 213.

A number of implementations have been described. Nevertheless, it will be understood that various modifications may be made without departing from the spirit and scope of this document. In particular, for example, implementations involving a balloon catheter for internal use have been described, but other types of catheters and devices can employ the concepts described herein, including devices that are configured for external use. As another example, a treatment component that is chilled through Joule-Thomson cooling (involving a liquid cryogenic agent flashing to a gas) is described, but other types of liquid or gas cooling processes can be employed. Specific procedures and body tissues are described, but the concepts described herein can be employed in other procedures and on other body tissue. Accordingly, other implementations are within the scope of the following claims.

What is claimed is:

1. A method of performing cryotherapy on a patient, the method comprising:
positioning an outer surface of a distal portion of a cryotherapy catheter in contact with body tissue to be treated;
performing a treatment phase comprising regulating a temperature of the outer surface at a treatment value for a first period of time, the first period of time selected to allow a cold front having a cold front temperature to propagate from the outer surface and through a therapeutic portion of a thickness of the body tissue, but not substantially beyond the thickness;
monitoring the progress of the cold front, and when the cold front has reached a desired distance from the outer surface of the cryotherapy catheter, then performing a recovery phase comprising allowing the temperature of the outer surface to warm up to a recovery value that is higher than the cold front temperature but substantially lower than a normal body temperature of the patient, wherein the recovery phase is performed until the cold front moves back through the body tissue to, or near, the outer surface of the cryotherapy catheter; and
performing an additional treatment phase for a second period of time, the second period of time selected to allow the cold front to propagate from the outer surface and through the therapeutic portion of the thickness, but not substantially beyond the thickness, wherein the performing the additional treatment phase includes monitoring the progress of the cold front, and stopping the additional treatment phase when the cold front reaches a desired distance from the outer surface of the cryotherapy catheter.

2. The method of claim 1, wherein performing the additional treatment phase comprises performing the additional treatment phase without repositioning the outer surface following the treatment phase and recovery phase.

3. The method of claim 1, further comprising performing multiple recovery phase-additional treatment phase sequences.

4. The method of claim 1, wherein the treatment value is −60° C. or colder.

5. The method of claim 1, wherein the recovery value is between −10° C. and +10° C.

6. The method of claim 1, wherein the cold front temperature is approximately −30° C.

7. The method of claim 1, wherein the recovery value is selected such that adhesion between the body tissue and the outer surface caused by performing the treatment phase is maintained through one or more recovery cycles.

8. The method of claim 1, wherein the distal portion comprises an inflatable balloon.

9. The method of claim 1, further comprising measuring a temperature at or in close proximity to the outer surface, wherein performing the recovery phase comprises performing the recovery phase for a period of time determined at least in part by the measured temperature.

10. The method of claim 1, wherein the second period of time is shorter than the first period of time.

11. The method of claim 1, wherein monitoring the progress of the cold front is performed directly by using a temperature probe.

12. The method of claim 1, wherein monitoring the progress of the cold front is performed indirectly by monitoring a detectable physiological event.

13. A cryotherapy catheter comprising:

an elongate member and a treatment component disposed at a distal end of the elongate member, the elongate member having lumens disposed therein to supply a cryogenic agent to an internal chamber of the treatment component and to channel exhaust from the internal chamber; and a controller programmed to control, during a cryotherapy procedure in which an outer surface of the treatment component is in contact with body tissue of a patient, a supply rate at which the cryogenic agent is supplied to the internal chamber and an exhaust rate at which exhaust is channeled from the internal chamber;

wherein the controller is programmed to (a) during a treatment phase of the cryotherapy procedure, regulate the supply and exhaust rates to cause a temperature on the outer surface to reach and be maintained at a treatment value for a first period of time that is selected to allow a cold front having a cold front temperature to propagate from the outer surface and through a therapeutic thickness of the body tissue, but not substantially beyond the therapeutic thickness; (b) monitor the progress of the cold front and determine when the cold front reaches a desired distance from the outer surface; (c) once the cold front reaches the desired distance, initiate a recovery phase of the cryotherapy procedure, during which the controller regulates the supply and exhaust rates to cause a temperature on the outer surface to warm up to a recovery value that is higher than the cold front temperature but substantially lower than the normal body temperature; (d) monitor a return of the cold font towards the outer surface; and (e) perform an additional treatment phase for a second period of time once the cold front has moved to or near the outer surface, the second period of time selected to allow the cold front to propagate from the outer surface and through the therapeutic thickness, but not substantially beyond the thickness.

14. The cryotherapy catheter of claim 13, further comprising a temperature sensor disposed on or in close proximity to the outer surface, wherein the controller is programmed to regulate the supply and exhaust rates during the recovery phase based at least in part on a temperature value measured by the temperature sensor.

15. The cryotherapy catheter of claim 13, wherein the treatment component comprises an inflatable balloon.

16. The cryotherapy catheter of claim 15, wherein a diameter of the elongate member is sized such that the inflatable balloon can be routed, in a deflated state, to the left atrium of an adult human patient.

17. The cryotherapy catheter of claim 15, wherein the inflatable balloon is configured to deliver, when inflated, cryotherapy to an ostium or antrum of a human patient's pulmonary vein.

18. The cryotherapy catheter of claim 17, wherein the controller is programmed to regulate the supply and exhaust rates during the treatment cycle in a manner that prevents damage to a phrenic nerve of the patient.

19. The cryotherapy catheter of claim 17, wherein the inflatable balloon is configured to deliver cryotherapy to at least one of the human patient's prostate, brain or varicose vein.

* * * * *